United States Patent
Rao et al.

(10) Patent No.: US 6,388,108 B1
(45) Date of Patent: May 14, 2002

(54) AMINOSTEROL COMPOUNDS AND USES THEREOF

(75) Inventors: Meena Rao, Monmouth Junction, NJ (US); Binyamin Feibush, Ambler; William Kinney, Newtown, both of PA (US); Michael Zasloff, Merion, PA (US); Lincoln Noecker, Gilbertsville, PA (US)

(73) Assignee: Genaera Corporation, Plymouth Meeting, PA (US)

( * ) Notice: Subject to any disclaimer, the term of this patent is extended or adjusted under 35 U.S.C. 154(b) by 0 days.

(21) Appl. No.: 09/762,999

(22) PCT Filed: Aug. 12, 1999

(86) PCT No.: PCT/US99/18322

§ 371 Date: May 29, 2001

§ 102(e) Date: May 29, 2001

(87) PCT Pub. No.: WO00/09137

PCT Pub. Date: Feb. 24, 2000

Related U.S. Application Data (60) Provisional application No. 60/096,337, filed on Aug. 12, 1998.

(51) Int. Cl.⁷ ......................... A61K 31/56; C07J 305/12
(52) U.S. Cl. ................. 552/521; 552/521; 552/506; 552/507; 552/527; 552/540; 552/542; 552/544; 552/548; 552/550; 552/552; 552/554; 552/557; 552/559; 552/582; 552/584; 552/583; 552/599; 514/182; 514/171

(58) Field of Search ................. 552/521, 507, 552/506, 524, 540, 542, 544, 548, 550, 551, 552, 554, 557, 559, 582, 583, 584, 599; 514/182

(56) References Cited

U.S. PATENT DOCUMENTS

| | | | |
|---|---|---|---|
| 5,192,756 A | 3/1993 | Zasloff et al. | 514/182 |
| 5,637,691 A | 6/1997 | Frye et al. | 540/106 |
| 5,721,226 A | 2/1998 | Frye et al. | 514/169 |
| 5,733,899 A | 3/1998 | Frye et al. | 514/169 |
| 5,763,430 A | 6/1998 | Zasloff | 514/169 |
| 5,840,936 A | 11/1998 | Zasloff et al. | 552/521 |
| 6,147,060 A | * 11/2000 | Zasloff et al. | 514/110 |

FOREIGN PATENT DOCUMENTS

| WO | 9824800 | * 6/1998 |
|---|---|---|

* cited by examiner

*Primary Examiner*—Sabiha Qazi
(74) *Attorney, Agent, or Firm*—Morgan, Lewis & Bockius LLP (57) ABSTRACT

Newly isolated aminosterol compounds and pharmaceutical compositions based on the aminosterol compounds are described. Methods for the treatment of various disorders, for example, a microbial infection, are also described.

24 Claims, 3 Drawing Sheets

AMINOSTEROL COMPOUNDS AND USES THEREOF

CROSS REFERENCE TO RELATED APPLICATIONS

This application is a 371 of PCT/US99/18322 filed Aug. 12, 1999.

This application claims benefit of priority under 35 U.S.C. §119(e) to U.S. Provisional Application Ser. No.: 60/096,337 filed Aug. 12, 1998, which is herein incorporated by reference in its entirety.

BACKGROUND OF THE INVENTION

1. Field of the Invention

The invention relates to newly isolated aminosterol compounds. Such aminosterol compounds are useful in a variety of pharmaceutical compositions as well as methods of treatment of various disorders such as, for example, a microbial infection.

2. Description of the Related Art

Over the past several years an increasing number of low molecular weight antibiotics have been isolated from diverse species of vertebrate animals such as frogs (Zasloff, 1987), pigs (Lee et al., 1989), mice (Ouellette et al., 1989) and humans (Jones et al., 1992). These antibiotic agents, including peptides (Steiner et al., 1981; Ganz et al., 1985; Zasloff, 1987), lipids (Kabara et al., 1977; Bibel et al., 1989) and alkaloids (Daly et al., 1987; Preusser et al., 1975), are believed to play a major role in host defense against environmental microbes.

The search for novel host defense agents led to the discovery of the aminosterol squalamine. Squalamine was isolated from the dogfish shark *Squalus acanthias* and proved to be active as a broad-spectrum antibiotic. U.S. Pat. No. 5,192,756. Squalamine also exhibited interesting anti-angiogenic and antitumor properties. Attempts to isolate large amounts of squalamine have now led to the discovery, isolation and purification of several new aminosterol compounds which are the subject of the present invention.

SUMMARY OF THE INVENTION

The invention provides newly isolated aminosterol compounds and pharmaceutically acceptable salts thereof.

The invention further provides pharmaceutical compositions comprising at least one aminosterol compound of the invention or a pharmaceutically acceptable salt thereof and a pharmaceutically acceptable carrier.

The invention further provides a method of treating a microbial infection comprising administering a therapeutically effective amount of at least one aminosterol compound of the invention or a pharmaceutically acceptable salt thereof.

DETAILED DESCRIPTION OF THE INVENTION

Figure 1:
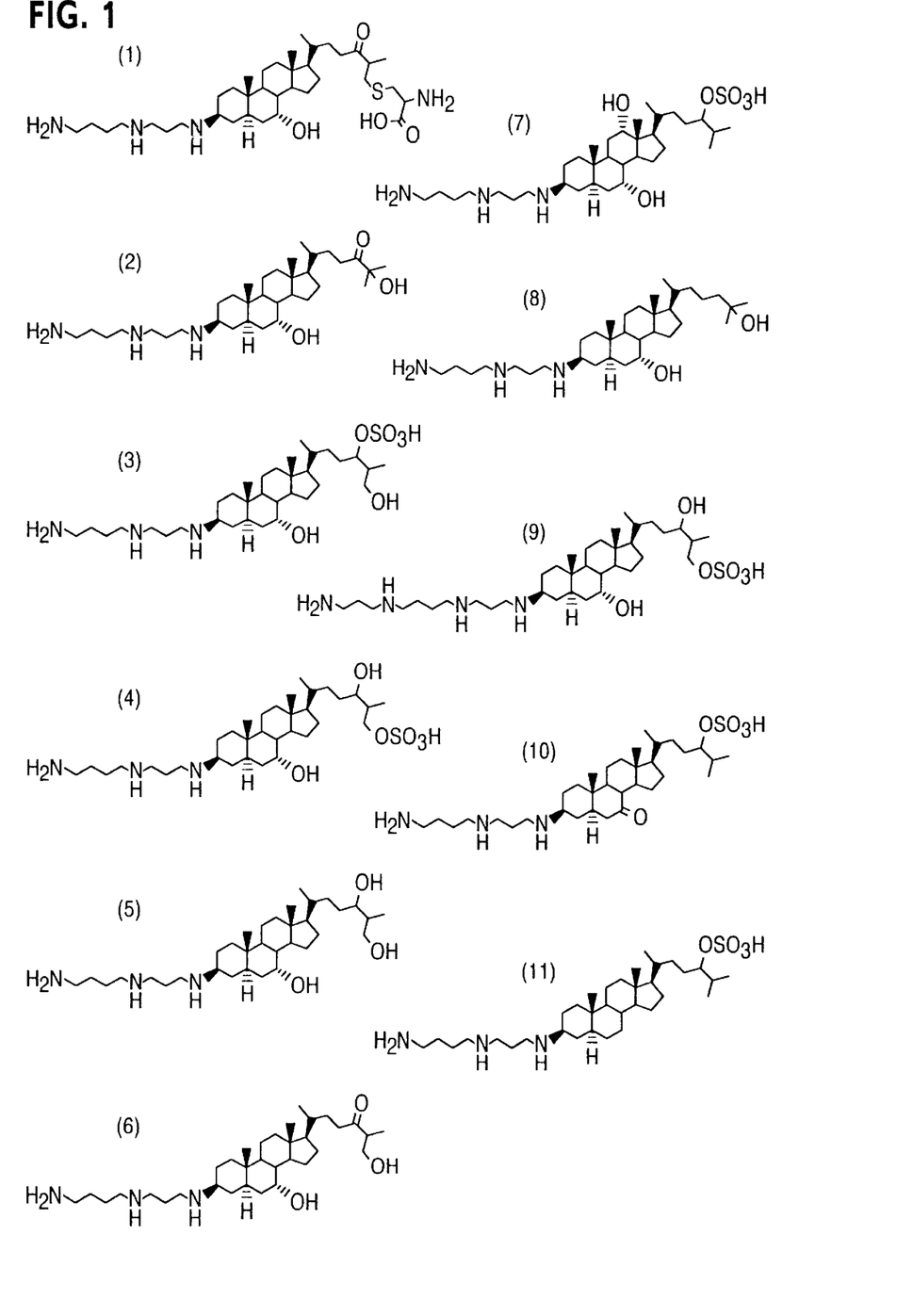
FIG. 1: Structure of aminosterol compounds (1)–(11).
Figure 2:
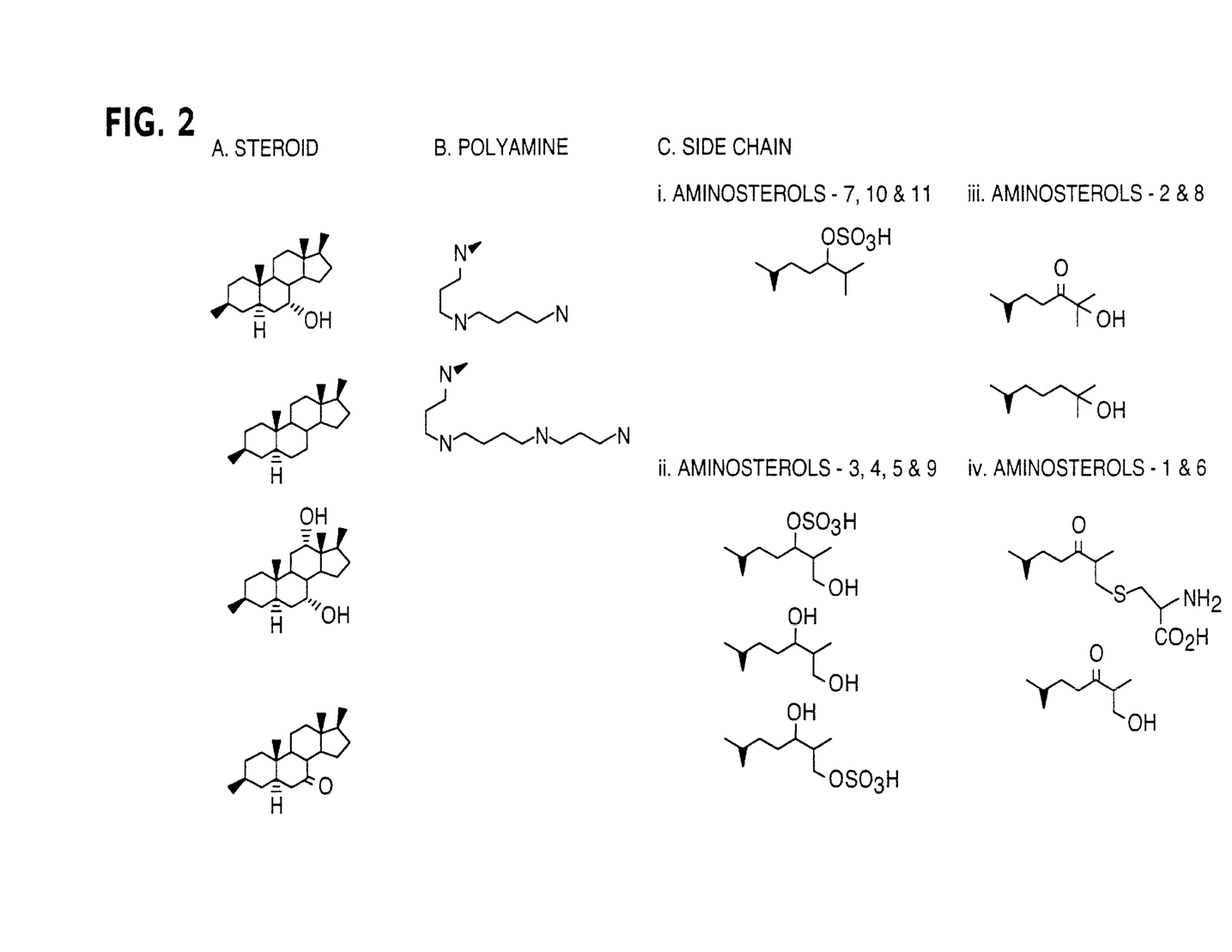
FIG. 2: Summary of structural diversity among aminosterol compounds (1)–(11).

The invention provides eleven newly isolated aminosterol compounds. The structure of the aminosterol compounds of the invention are illustrated in FIG. 1. As illustrated in FIG. 2, each of the aminosterol compounds of the invention has a steroid nucleus, a polyamine moiety attached to the steroid nucleus and a cholestane-related side chain. The steroid nucleus of an aminosterol compound of the invention has a trans AB ring junction (Wehrli et al., 1993). The C7 and/or the C12 position of an aminosterol compound of the invention (see FIG. 3 for numbering of the aminosterol compounds) may be further substituted with a hydroxyl group or a carbonyl moiety. For example, aminosterol compound (7) is hydroxylated at both the C7 and C12 positions and aminosterol compound (10) is substituted with a carbonyl moiety at the C7 position. Aminosterol compound (11) is substituted at neither the C7 or C12 position.

The aminosterol compounds of the invention are substituted equatorially at the C3 position of the steroid nucleus with a polyamine moiety. The polyamine moiety may be either a spermidine moiety (i.e. —NH—$(CH_2)_3$—NH—$(CH_2)_4$—$NH_2$) or a spermine moiety (i.e. —NH—$(CH_2)_3$—NH—$(CH_2)_4$—NH—$(CH_2)_3$—$NH_2$). As illustrated in FIG. 1, aminosterol compounds (1)–(8) and (10)–(11) contain a spermidine moiety at the C3 position. Aminosterol compound (9) contains a spermine moiety at the C3 position.

In a preferred embodiment of the invention, the aminosterol compounds of the invention may be obtained in isolated or purified form the tissues (e.g. liver tissue) of the dogfish shark, *Squalus acanthias*.

Isolation

Fresh ground liver of the dogfish shark *Squalus acanthias* is treated with about 12% aqueous acetic acid at about 75° C. for about one hour. Next, ammonium sulfate and about 95% ethanol are added followed by vigorous agitation for about five minutes. The resulting suspension is then allowed to phase separate (i.e. separate into an organic phase and an aqueous phase) for about six days at about ambient temperature. The aqueous phase is then separated and filtered through cheesecloth. The filtrate is then slowly stirred with XAD-16 resin (commercially available from Supelco of Bellefonte, Pa.) for about twenty hours. The resin is then collected, washed with water and resuspended in about 70% ethanol for approximately twenty minutes. Removal of the resin leaves an alcohol solution containing aminosterol compounds (1)–(11) of the invention.

Purification and Analysis

The alcohol solution containing aminosterol compounds (1)–(11), as described above, is then filtered through a five micron polypure DCF filter (commercially available from Gelman Sciences of Ann Arbor, Mich.). The filtrate is then loaded onto a propylsulfonic acid column (commercially available from JT Baker of Phillipsburg, N.J.). The column is then washed with about 20% isopropyl alcohol until an adsorption reading of about 254 nanometers (A254) reaches a constant level. The column may then be washed with about 0.4 M potassium acetate in about 10% isopropyl alcohol until the A254 again reaches a constant level. The aminosterol compounds of the invention are then eluted from the column with either an about 3.6 M or about 4.5 M potassium acetate (about pH 4) in about 10% isopropyl alcohol.

The about 3.6 M and about 4.5 M potassium acetate eluates are separately filtered through an about 0.2 micron Sartopure GF capsules (commercially available from Sartorius of Edgewood, N.Y.), diluted with water to about a 1.0 M salt concentration and loaded onto a YMC-ODS column (commercially available from YMC of Wilmington, N.C.). Two buffers, Buffer A and Buffer B, are used to elute the aminosterols of the invention from the column. Buffer A consists of about 0.1% trifluoroacetic acid in water while Buffer B consists of about 0.1% trifluoroacetic acid in acetonitrile. The column is first washed with Buffer A, then with about 25% Buffer B solution. The aminosterols of the invention are then eluted from the column using a gradient from about 25–34% Buffer B followed by a gradient from about 34–40% Buffer B.

The fractions eluted with the about 25–34% Buffer B gradient system and the fractions eluted with the about 34–40% Buffer B gradient system may then be loaded onto a second propylsulfonic acid column. The propylsulfonic acid column is washed and the aminosterol compounds of the invention are eluted with the about 3.6 M and about 4.5 M potassium acetate solutions, each as described above. The eluates of the about 3.6 M and about 4.5 M potassium acetate solutions are collected and analyzed by thin-layer chromatography and HPLC. The eluates may be ultra-filtered through a spiral membrane cartridge with a three kiloDalton cutoff (commercially available from Amicon of Woburn, Mass.) to remove higher molecular weight residual pigments and proteins. The resulting permeate may then be loaded on YMC-ODS or Dynamax column (commercially available from Ranin of Woburn, Mass.), washed with Buffer A, as described above, and eluted with an appropriate gradient of Buffer B, as described above. The eluates may be further analyzed on an analytical reverse phase (RP) column using pre-column o-phthalaldehyde (OPA) derivatization and further purified on a Phenomenex Luna C18, Phenomenex phenyl-hexyl or Microsorb C18 column (commercially available from Woburn, Mass.).

As a result of such isolation and purification, a substantially homogeneous composition of each aminosterol compound of the invention, as described herein, may be prepared. "Substantially homogeneous composition" is defined as a composition that is equal to or greater than about 95% pure excluding salt counter ions, as demonstrated by thin layer chromatography, o-phthalaldehyde analysis and NMR. Aminosterol compounds (1), (4) and (7) may be isolated and purified from the liver tissue of the common dogfish shark, *Squalus acanthias*, in amounts of about 0.5–2.5 milligrams per kilogram liver tissue and are designated as the "Major Aminosterols." Aminosterol compounds (2), (3), (5), (6), (8), (9), (10) and (11) may be isolated and purified in amounts of less than about 0.05 milligrams per kilogram of liver tissue and are designated as the "Minor Aminosterols." The aminosterol compounds of the invention have been numbered one (1) through eleven (11) based on their order of elution under high performance liquid chromatography (HPLC) conditions, as described herein.

Analytical Data

The Major Aminosterols

The structures of the Major Aminosterols, i.e. aminosterol compounds (1), (4) and (7), was determined using mass spectroscopy and two-dimensional proton ($^1$H) NMR and carbon-13 ($^{13}$C) NMR experiments, heteronuclear chemical shift correlation spectra (HMQC), proton detected carbon-proton multiple bond correlation spectra (HMBC), and phase sensitive correlated spectroscopy (COSY). The results were compared against similar data for squalamine for structure determination of the aminosterols. The $^1$H NMR and $^{13}$C NMR data of the Major Aminosterols are summarized in Tables 1 and 2, respectively. The mass spectroscopy data for the aminosterol compounds of the invention are summarized in Table 4.

As shown in Table 4, aminosterol compound (1) gave a positive ion mass by fast atom bombardment mass spectroscopy (FAB) [M$^+$H]$^+$ at m/z 665 and fragment ions at m/z 578 and m/z 546, representing the loss of α-amino propionic acid and cysteine, respectively. Aminosterol compound (1) also gave a positive ion mass by high-resolution mass spectroscopy (HRMS) (FAB) [M$^+$H]$^+$ at m/z 665.5043, consistent with the calculated value of 665.5039.

Aminosterol compound (4) exhibited a positive ion mass by matrix-assisted laser desorption-ionization mass spectroscopy (MALDI) [M$^+$H]+$^+$ at m/z 645.5 and fragment ion at m/z 566.6 and a negative mass (FAB) [M$^-$H]$^-$ at m/z 642.3. Aminosterol compound (4) gave a negative ion mass by high-resolution electrospray mass spectroscopy (ES) [M$^-$H]$^-$ at m/z 642.4502, consistent with the calculated value of 642.4515.

Figure 3:
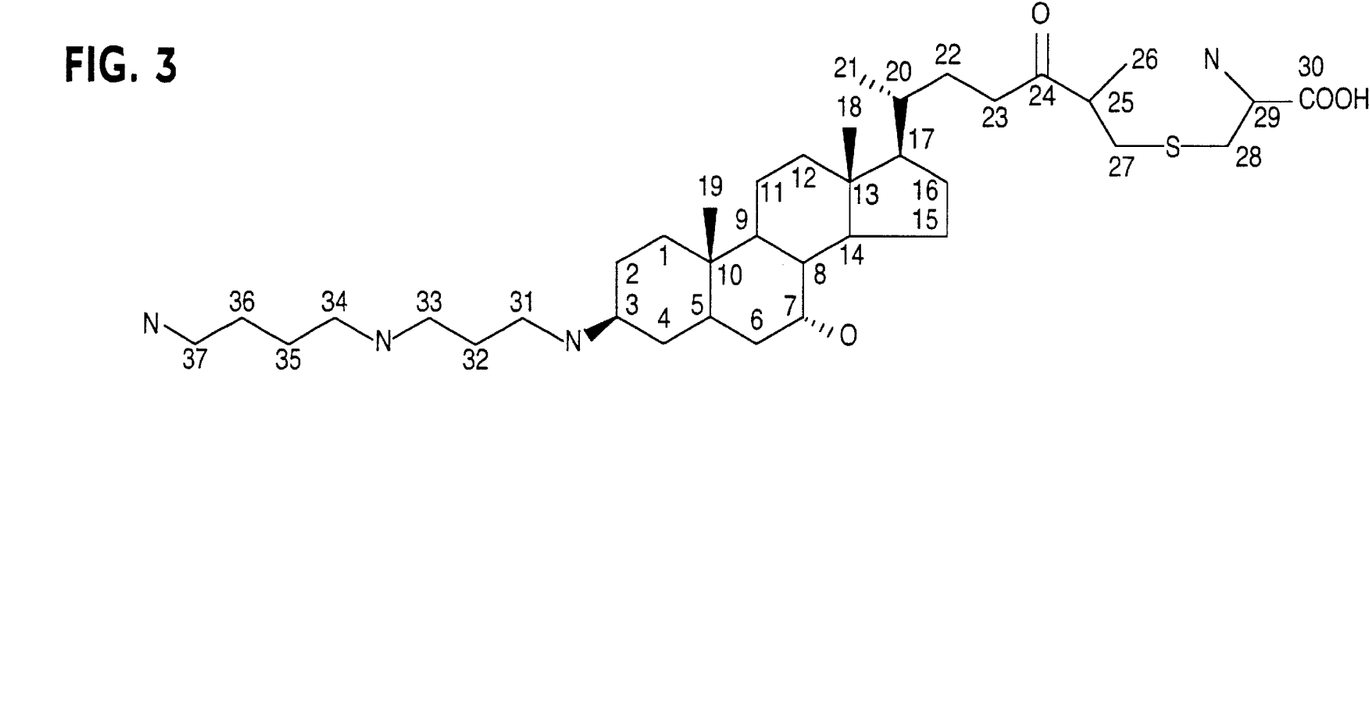
FIG. 3: General numbering scheme for aminosterol compounds (1)–(11).

As shown in Table 1, the one-dimensional $^1$H NMR data for aminosterol compounds (1) and (4) indicated the characteristic appearance of a steroid, with two singlets for the angular methyl groups at the C18 and C19 positions and two doublets for methyl groups at the C21 and C26 positions (see FIG. 3). The $^1$H NMR data for aminosterol compound (4) also show the presence and overlapping of doublets for the methyl groups at the C21 and C26 positions. In addition, the C24 keto group of aminosterol compound (1) displays a characteristic multiplet between δ2.4–2.8, integrating for two protons identified as the methylene protons at the C23 position. Aminosterol compound (1) also displays a multiplet for the α-proton of cysteine at δ3.96, while the hydrogen (H) at the C24 position of aminosterol compound (4) produced a similar multiplet at δ3.44. The hydroxyl group located at the C27 position of aminosterol compound (4) is sulfated (i.e. a —OSO$_3$H group) and hence the hydrogens at the C26 protons are diastereotopic and display a distinct splitting pattern of a doublet of doublets. The spermidine moiety at the C3 position integrates typically for nine protons, eight methylene protons immediately adjacent to an NH group of spermidine and the C3 axial proton. For aminosterol compound (1), the four methylene protons at C27 and C28 adjacent to the sulfur atom also overlap in this region, in addition to the CH proton at C25. The rest of the steroid protons, including the hydrogen at the C7 position at δ3.80, are identical to squalamine.

The $^{13}$C NMR chemical shifts of aminosterol compounds (1), (4), and (7) summarized in Table 2 were assigned using a number of experiments including distortion enhanced by polarization transfer (DEPT-135), HMQC, HMBC and phase sensitive double quantum filtered correlated spectroscopy (DQF COSY) and also by comparison with squalamine. HMBC long-range $^1$H and $^{13}$C connectivities were especially vital to confirm the structures of the aminosterol compounds of the invention. In aminosterol compound (1), the following correlations establish that the cysteine sulfur atom is connected to the C27 carbon: C24 carbonyl carbon at δ216.27 and the C26 carbon at δ17.14 display correlations to the protons at the C27 position at δ2.62 and δ2.85; the C27 carbon at δ35.49 through S to the protons at the C28 position at δ2.97 and δ3.14; the C28 carbon at δ34.21 through S to the protons at the C27 position at δ2.62 and δ2.85; the C29 cysteine α-carbon at δ54.47 to the protons at the C28 position at δ2.97 and δ3.14. Aminosterol compound (4) is a 24-hydroxy aminosterol and its C24 hydroxy carbon at δ74.17, the C25 carbon at δ40.65 and the C26 carbon at δ14.35 all display correlations to the protons a the C27 position at δ3.96 and δ4.12, thus establishing the position of sulfate with respect to the 24-hydroxyl group.

Aminosterol compound (7) has an additional hydroxyl group in comparison to squalamine. The loss of sulfur trioxide (80 amu) and sulfuric acid (98 amu) in the positive ion mass spectra, is characteristic of most sulfated aminosterols. Accordingly, aminosterol compound (7) displays a (MALDI) [M⁺H]⁺ at m/z 645.4 with fragments at m/z 566.3 and m/z 547.2 for the loss of sulfur trioxide and sulfuric acid and a negative mass (MALDI) [M⁻H]⁻ at +m/z 643.6. Aminosterol compound (7) also displays a positive ion mass by high-resolution mass spectroscopy (FAB) [M⁺H]⁺ at m/z 644.4687, consistent with the calculated value of 644.4672. The one-dimensional ¹H NMR spectra of aminosterol compound (7) displays the characteristic two singlets for the angular methyl groups at the C18 and C19 positions, overlapping doublets for the methyl groups at the C26 and C27 positions and a doublet for the methyl group at the C21 position. Aminosterol compound (7) also displays a typical NMR pattern for the spermidine side chain that integrates for nine protons and a singlet for the proton at the C7 position at δ3.81. In addition, aminosterol compound (7) displays a multiplet integrating for one proton at δ4.14 at the C24 position. An additional singlet for this compound is present at δ3.95 and represents the hydrogen at the C12 position. The presence of a hydroxyl group at the C12 position was apparent from the HMBC correlation experiment, where the angular methyl C18 resonance displays correlation to the hydroxyl group. It was determined to be an axial hydroxyl group as that found at the C7 position from the DQF phase sensitive COSY experiment due to the lack of diaxial coupling between the protons at C11 and C12 positions. The presence of a hydroxyl group at the C12 position would be expected to affect the ¹³C NMR chemical shifts of C11, C13, C14 and C17 by moving the C14 and C17 signals upfield and the C11 and C13 signals downfield.

All the aminosterols described thus far have spermidine substituted at the C3 position in the equatorial position confirmed by the large diaxial coupling constants observed for the axial proton at the C3 position with the axial proton at the C4 position and the axial position at the C2 position in a phase sensitive DQF COSY experiment. It is believed that since all the aminosterols, including squalamine, originated from the same natural source, the spermidine is attached to the steroid nucleus at its three-carbon end, as was shown for squalamine through TOCSY (total correlation spectroscopy) correlations.

The Minor Aminosterols

The structures of the Minor Aminosterols, i.e. aminosterol compounds (2), (3), (5), (6), (8), (9), (10) and (11), were determined by mass spectroscopy and ¹H NMR. The results, summarize in, respectively, Tables 3 and 4, were compared against similar data for squalamine.

Aminosterol compounds (2) and (8) are both hydroxylated at the C25 position of the cholestane-related side chain. Aminosterol compound (2) is substituted with a keto group at the C24 position. The mass spectral data of aminosterol compounds (2) and (8) display only a single mass in the positive mode (MALDI) [M⁺H]⁺ at m/z 562.1 and m/z 547.8, respectively. Aminosterol compound (2) and (8) also display a positive ion mass by high-resolution mass spectroscopy (FAB) [M⁺H]⁺ at m/z 562.4966 and 548.5165, respectively. These values are consistent with the calculated values of 562.4947 and 548.5155. The ¹H NMR spectra of these aminosterols clearly identify the steroid region with singlets for angular methyl protons at the C18 and C19 positions and a doublet for the methyl group at the C21 position. The isopropyl protons produce a singlet integrating for six protons down field at δ1.28 for aminosterol compound (2) and δ1.20 for aminosterol compound (8), due to the substitution at the C25 position. In addition, aminosterol compound (2) produces a multiplet integrating for two protons at δ2.65 for the methylene protons at the C23 position, typical of 24-keto aminosterols. The C7 proton adjacent to the hydroxyl group in these aminosterols is a singlet at δ3.79 for aminosterol compound (2) and δ3.88 for aminosterol compound (8), while the polyamine region at the C3 position is characteristic of spermidine.

Minor Aminosterol compounds (3), (5), and (6). Aminosterol compound (3) is a regioisomer of the major aminosterol compound (4) and although identical in its mass, it can be readily distinguished from aminosterol compound (4) by its one-dimensional ¹H NMR spectrum. The steroid region for aminosterol compounds (3) and (4) produce a characteristic pattern, singlets for the angular methyl groups at the C18 and C19 positions and overlapping doublets for methyl groups at the C21 and C26 positions. In aminosterol compound (3), the hydroxyl group at the C27 position is not sulfated, hence the protons at the C27 position resonate upfield at δ3.47 and δ3.70 as a distinct doublet of doublets, as opposed to δ3.84 and δ4.01 for aminosterol compound (4), in which the hydroxyl group at the C27 position is sulfated. The 24-hydroxyl group is sulfated in aminosterol compound (3) and resonates at δ4.13 as opposed to δ3.33 in aminosterol compound (4). Aminosterol compound (3) displays a (MALDI) [M⁺H]⁺ at m/z 645.1 with fragments at m/z 565.3 and m/z 546.9 and a negative mass (MALDI) [M⁻H]⁻ at m/z 642.4. Aminosterol compound (3) also displays a negative ion mass by high-resolution mass spectroscopy (ES) [M⁻H]⁻ at m/z 642.4506, consistent with the calculated value of 642.4515.

Aminosterol compound (5) is hydroxylated at the C24 and C27 positions and neither of these hydroxyl groups are sulfated. The ¹H NMR spectra for aminosterol compound (5) also displays two singlets for the angular methyl groups at the C18 and C19 positions and two distinct separated doublets for methyl groups at the C21 and C27 positions. As in aminosterol compound (3), the hydroxyl group at the C27 position is not sulfated hence the protons at the C27 position resonate upfield at δ3.50 and δ3.65. As the 24-hydroxyl in aminosterol compound (5) is also not sulfated, it resonates upfield at δ3.44. Aminosterol compound (5) displays a (MALDI) [M⁺H]⁺ at m/z 565.5, consistent with the calculated value of 564.5.

One-dimensional ¹H NMR can readily distinguish aminosterol compound (6) from aminosterol compound (5). The angular methyl groups at the C18 and C19 positions are singlets, while those at the C21 and C26 positions are well-separated doublets. Aminosterol compound (6) is a 24-keto aminosterol and typical of keto aminosterols, the methylene protons at the C23 position resonate at δ2.53. The proton at the C25 position which is usually buried in the polyamine region in most keto aminosterols is separated from the polyamine region as a multiplet at δ2.78 as is the case in aminosterol compound (6). The C27 position of aminosterol compound (6) is hydroxylated and hence the protons at the C27 position are diastereotopic and split as a doublet of doublets at δ3.55 and δ3.68. In addition, aminosterol compound (6) displays a (MALDI) [M⁺H]⁺ at m/z 562.1. Aminosterol compound (6) also displays a positive ion mass by high-resolution mass spectroscopy (FAB) [M⁺H]⁺ at m/z 562.4954, consistent with the calculated value of 562.4948.

Structure of minor aminosterol compound (9), (10), and (11). Aminosterol compound (9) in this collection is the only compound that has a spermine moiety instead of spermidine moiety conjugated to the steroid at the C3 position. Aminosterol compound (9) is structurally identical to aminosterol compound (4) in the cholestane-related side chain. It differs however in the polyamine region, which integrates for thirteen protons, representing 12 methylene protons adjacent to the spermine NH's and a C3 axial proton, and displays greater symmetry for the symmetrical spermine. Aminosterol compound (9) displays a negative ion mass by high-resolution mass spectroscopy (ES) [M⁻H]⁻ at m/z 699.5093, consistent with the calculated value of 699.5094.

Aminosterol compound (10) has a mass (FAB) [M⁺H]⁺ two less than squalamine at m/z 626.5 and a fragment ion at m/z 528.5. Aminosterol compound (10) also displays a positive ion mass by high-resolution mass spectroscopy (FAB) [M⁺H]⁺ at m/z 626.4566, consistent with the calculated value of 626.4532. The one-dimensional ¹H NMR spectra displays a singlet for the angular methyl at the C18 position and a singlet for the methyl group at the C19 position at δ1.16, shifted downfield by the keto group at the C7 position. The doublets for the methyl groups at the C21, C26 and C27 positions overlap at δ0.95, which in all integrate for nine protons. As in squalamine, a multiplet integrating for one proton at δ4.15 was assumed to be the proton at the C24 position, shifted downfield due to sulfonation.

Aminosterol compound (11) displays a positive ion mass (MALDI) [M⁻H]⁻ at m/z 612.2 with fragment ions at m/z 522.6 and m/z 514.8 for the loss of sulfur trioxide and sulfuric acid and a negative ion mass (MALDI) [M⁻H]⁻ at m/z 611.50. Aminosterol compound (11) also displays a positive ion mass by high-resolution mass spectroscopy (FAB) [M⁺H]⁺ at m/z 612.4747, consistent with the calculated value of 612.4774. Its ¹H NMR spectrum is identical to squalamine except the C7 proton at δ3.75 seen in squalamine is not present.

TABLE 1

Selected ¹H NMR Data of Major Aminosterol Compounds (1), (4), and (7)

| Position | Aminosterol (1) | Aminosterol (4) | Aminosterol (7) |
|---|---|---|---|
| 1ax | 1.12 | 1.14 | 1.18 |
| 1eq | 1.86 | 1.86 | 1.83 |
| 2ax | 1.56 | 1.58 | 1.56 |
| 2eq | 1.96 | 2.00 | 2.04 |
| 3 | 3.13 | 3.14 | 3.16 |
| 4ax | 1.43 | 1.43 | 1.42 |
| 4eq | 1.61 | 1.65 | 1.65 |
| 5 | 1.74 | 1.76 | 1.75 |
| 6ax | 1.53 | 1.54 | 1.54 |
| 6eq | 1.45 | 1.46 | 1.46 |
| 7 | 3.80 (s) | 3.80 (1,s) | 3.81 (1,s) |
| 8 | 1.44 | 1.40 | 1.47 |
| 9 | 1.23 | 1.29 | 1.59 |
| 11ax | 1.35 | 1.34 | 1.58 |
| 11eq | 1.54 | 1.54 | 1.54 |
| 12ax | 1.13 | 1.18 | |
| 12eq | 1.98 | 2.00 | 3.95 (1,s) |
| 14 | 1.43 | 1.43 | 1.96 |
| 15a, 15b | 1.78, 1.14 | 1.77, 1.12 | 1.76, 1.11 |
| 16a, 16b | 1.35, 1.89 | 1.32, 1.93 | 1.31, 1.90 |
| 17 | 1.14 | 1.18 | 1.82 |
| 18 | 0.70 (3,s) | 0.71 (3,s) | 0.72 (3,s) |
| 19 | 0.86 (3,s) | 0.87 (3,s) | 0.85 (3,s) |
| 20 | 1.43 | 1.44 | 1.42 |
| 21 | 0.94 (3,d) | 0.97 (3,d) | 1.02 (3,d) |
| 22a, 22b | 1.23, 1.70 | 1.10, 1.90 | 1.31, 1.45 |
| 23a, 23b | 2.54, 2.54 | 1.50, 1.44 | 1.71, 1.51 |
| 24 | | 3.44 (1,m) | 4.14 (1,m) |
| 25 | 2.89 | 1.85 | 2.08 |
| 26 | 1.15 (3,d) | 0.99 (3,d) | 0.93 (3,d) |
| 27a, 27b | 2.62, 2.85 | 3.96 (1,dd), 4.12 (1,dd) | 0.96 (3,d) |
| 28a, 28b | 2.97, 3.14 | 3.16 | 3.19 |
| 29 | 3.96 (1,m) | 2.11 | 2.16 |
| 30 | | 3.16 | 3.16 |
| 31 | 3.15 | 3.09 | 3.08 |
| 32 | 2.11 | 1.80 | 1.82 |

TABLE 1-continued

Selected ¹H NMR Data of Major Aminosterol Compounds (1), (4), and (7)

| Position | Aminosterol (1) | Aminosterol (4) | Aminosterol (7) |
|---|---|---|---|
| 33 | 3.15 | 1.76 | 1.76 |
| 34 | 3.08 | 2.99 | 2.99 |
| 35 | 1.80 | | |
| 36 | 1.75 | | |
| 37 | 2.98 | | |

TABLE 2

Selected ¹³C Data of Major Aminosterol Compounds (1), (4), and (7)

| Position | Aminosterol (1) | Aminosterol (4) | Aminosterol (7) |
|---|---|---|---|
| 1 | 37.72 | 37.80 | 37.57 |
| 2 | 26.03 | 26.07 | 25.93 |
| 3 | 59.03 | 59.12 | 59.15 |
| 4 | 32.16 | 31.14 | 32.09 |
| 5 | 38.66 | 38.68 | 38.66 |
| 6 | 37.72 | 37.80 | 37.71 |
| 7 | 68.39 | 68.38 | 68.40 |
| 8 | 41.05 | 41.14 | 41.21 |
| 9 | 46.90 | 46.85 | 40.42 |
| 10 | 36.79 | 36.94 | 36.48 |
| 11 | 22.14 | 22.23 | 29.82 |
| 12 | 40.99 | 41.14 | 73.84 |
| 13 | 43.83 | 43.88 | 47.52 |
| 14 | 51.78 | 51.79 | 43.45 |
| 15 | 24.58 | 24.73 | 24.25 |
| 16 | 29.31 | 29.55 | 28.78 |
| 17 | 57.63 | 58.01 | 48.27 |
| 18 | 12.42 | 12.56 | 13.12 |
| 19 | 11.54 | 11.68 | 11.39 |
| 20 | 36.86 | 37.35 | 37.23 |
| 21 | 19.11 | 19.47 | 18.25 |
| 22 | 30.82 | 33.32 | 33.02 |
| 23 | 40.12 | 32.15 | 28.04 |
| 24 | 216.27 | 74.17 | 86.26 |
| 25 | 47.53 | 40.65 | 32.30 |
| 26 | 17.14 | 14.35 | 18.38 |
| 27 | 35.49 | 71.68 | 18.18 |
| 28 | 34.21 | 46.07 | 45.98 |
| 29 | 54.47 | 24.61 | 24.61 |
| 30 | 171.69 | 43.05 | 42.97 |
| 31 | 46.03 | 48.72 | 48.38 |
| 32 | 24.58 | 24.36 | 24.19 |
| 33 | 42.91 | 25.70 | 25.93 |
| 34 | 48.94 | 40.16 | 40.06 |
| 35 | 24.36 | | |
| 36 | 25.70 | | |
| 37 | 40.12 | | |

TABLE 3

Selected $^1$H NMR (400 MHZ In CD$_3$OD) data of Minor Aminosterols (2)–(3), (5)–(6), and (8)–(11)

| Position | (2) | (3) | (5) | (6) | (8) | (9) | (10) | (11) |
|---|---|---|---|---|---|---|---|---|
| 7 | 3.79 (1,s) | 3.80 (1,s) | 3.80 (1,s) | | 3.88 (1,s) | 3.82 (1,s) | | |
| 18 | 0.69 (3,s) | 0.72 (3,s) | 0.70 (3,s) | 0.69 (3,s) | 0.74 (3,s) | 0.73 (3,s) | 0.71 (3,s) | 0.69 (3,s) |
| 19 | 0.85 (3,s) | 0.87 (3,s) | 0.86 (3,s) | 0.86 (3,s) | 0.89 (3,s) | 0.88 (3,s) | 1.16 (3,s) | 0.85 (3,s) |
| 21 | 0.94 (3,d) | 0.95 (3,d) | 0.91 (3,d) | 0.93 (3,d) | 1.00 (3,d) | 0.97 (3,s) | 0.95 (3,d) | 0.93 (3,m) |
| 23 | 2.65 (2,m) | | | 2.53 (1,m) | | | | |
| 24 | | 4.13 (1,m) | 3.44 (1,m) | | | 3.45 (1,m) | 4.15 (1,m) | 4.09 (1,s) |
| 25 | | | | 2.78 (1,m) | | | | |
| 26 | 1.28 (6,s) | 0.96 (3,d) | 0.95 (3,d) | 1.01 (3,d) | 1.20 (6,s) | 1.01 (3,d) | 0.95 (6,m) | 0.93 (6,m) |
| 27a | | 3.47 (1,dd) | 3.50 (1,dd) | 3.55 (1,dd) | | 4.14 (1,dd) | | |
| 27b | | 3.70 (1,dd) | 3.65 (1,dd) | 3.68 (1,dd) | | 3.95 (1,dd) | | |

TABLE 4

Mass Spectroscopy Data for Aminosterol Compounds (1)–(11)

| | formula | MALDI M + 1 | MALDI M − 1 | FAB | HRMS | RT |
|---|---|---|---|---|---|---|
| 1 | $C_{37}H_{68}N_4O_4S$ | | | 665 (100%)<br>578 (38%)<br>546 (17%) | 665.5043 (e)<br>665.5039 (c) | 22.9 |
| 2 | $C_{34}H_{63}N_3O_3$ | 562.1 (100%) | | | 562.4966 (e)<br>562.4947 (c) | 20.1 |
| 3 | $C_{34}H_{65}N_3O_6S$ | 645.1 (91%)<br>565.3 (34%)<br>546.9 (100%) | 642.4 (100%) | | 642.4506 (e)<br>642.4515 (c) | 13.2 |
| 4 | $C_{34}H_{65}N_3O_6S$ | 645.5 (100%)<br>566.6 (62%) | | 642.3 (100%) | 642.4502 (e)<br>642.4515 (c) | 13.5 |
| 5 | $C_{34}H_{65}N_3O_3$ | 565.5 (e) (100%)<br>564.5 (c) | | | | 18.2 |
| 6 | $C_{34}H_{63}N_3O_3$ | 562.1 (100%) | | | 562.4954 (e)<br>562.4948 (c) | 19.4 |
| 7 | $C_{34}H_{65}N_3O_6S$ | 645.4 (100%)<br>566.3 (29%)<br>547.2 (94%) | 643.6 (100%) | | 644.4687 (e)<br>644.4672 (c) | 16.0 |
| 8 | $C_{34}H_{65}N_3O_2$ | 547.8 (100%) | | | 548.5165 (e)<br>548.5155 (c) | 17.4 |
| 9 | $C_{37}H_{72}N_4O_6S$ | | 700.1 (100%) | | 699.5093 (e)<br>699.5094 (c) | 15.1 |
| 10 | $C_{34}H_{63}N_3O_5S$ | | | 626.5 (35%)<br>528.5 (100%) | 626.4566 (e)<br>626.4532 (c) | 18.6 |
| 11 | $C_{34}H_{65}N_3O_4S$ | 612.2 (52%)<br>522.6 (100%)<br>514.8 (52%) | 611.5 (100%) | | 612.4747 (e)<br>612.4774 (c) | 22.5 |

RT - OPA HPLC Retention Time (minutes).
(e) Experimental value, (c) Calculated value.

In another preferred embodiment of the invention, the aminosterol compounds of the invention may be obtained in isolated or purified form by chemical synthetic means. The aminosterol compounds of the invention may be synthesized and isolated or purified by any means known in the art. U.S. Pat. Nos. 5,637,691, 5,721,226, 5,733,899, 5,763,430, 5,792,635, 5,795,885, 5,840,740, 5,840,936, 5,847,172, 5,856,535 and 5,874,597 and WO 94/19366. Synthesized and isolated or purified derivatives of the aminosterol compounds of the invention are also envisioned. For example, aminosterol compounds (1)–(8) and (10)–(11) may be synthesized in which the spermidine polyamine moiety at the C3 position is replaced with a spermine polyamine moiety. Similarly, aminosterol compound (9) may be synthesized in which the spermine polyamine moiety at the C3 position is replaced with a spermidine polyamine moiety.

According to the invention, pharmaceutically acceptable salts of each of the aminosterol compounds (1)–(11) or derivatives thereof each as described above, may be prepared by any means known in the art. Such salts include, but are not limited to, sodium, potassium, ammonium, chloride, triflouroacetate, lactate and acetate salts.

The invention also provides a pharmaceutical composition comprising at least one of the aminosterols of the invention or a derivative thereof as an active ingredient present in a therapeutically effective amount and a pharmaceutically acceptable carrier. The aminosterol compound or derivative thereof are each as described above and the pharmaceutically acceptable carrier may be any such carrier known in the art, preferably a pharmaceutically acceptable, non-toxic sterile carrier as would be recognized by one of skill in the art. Also as recognized by one of skill in the art, a "therapeutically effective amount" will be determined on a case by case basis. Factors to be considered include, but are not limited to, the disorder to be treated and the physical characteristics of the one suffering from the disorder. Accordingly, a "therapeutically effective amount" will be best determined through routine experimentation.

Preferably, a pharmaceutical composition of the invention contains between about 0.001 and about 5.0% by weight, preferably between about 0.01 to about 1.0% by weight of an aminosterol compound of the invention. A pharmaceutical composition of the invention may be prepared by means known in the art.

A pharmaceutical composition of the invention may be, for example, a solid (e.g. powder, pill, tablet), liquid (e.g. syrup, elixir), suspension, or emulsion and may be adapted for systemic administration. Other modes of administration of a pharmaceutical composition of the invention include, depending on the state of the pharmaceutical composition, methods known in the art such as, but not limited to, oral administration, topical application, parenteral, intravenous, intranasl, intraocular, intracranial, deposition under the skin, intramuscular or intraperitoneal injection. Preferably, a pharmaceutical composition of the invention is applied as a topical formulation. Any common topical formulation such as, for example, a solution, suspension, gel, ointment or salve may be used. A topical formulation of a pharmaceutical composition of the invention may also be administered as a powder or spray, particularly in aerosol form. Preparation of such topical formulations are well known in the art as exemplified in Remington's Pharmaceutical Sciences, 19th edition, Mack Publishing Company, 1995.

Although the amount of pharmaceutical composition systemically administered will be determined on a case by case basis, as described above, preferably between about 0.01–100 milligrams per kilogram body weight per day, more preferably, between about 0.1–10 milligrams per kilogram body weight per day, will be administered.

According to the invention, additional therapeutic agents may be added to a pharmaceutical composition of the invention. The therapeutic agent may be any synthetic or naturally occurring biologically active therapeutic agent known in the art. Examples of suitable therapeutic agents include, but are not limited to, antibiotics, steroids, genomic DNA, cDNA, mRNA, antisense oligonucleotides, plasmids, peptides, peptide fragments, small molecules and other biologically active macromolecules such as, for example, proteins and enzymes.

The aminosterol compounds of the invention exhibit a broad range of antimicrobial activity or potent antibiotic activity against a plurality of microorganisms or microbes including, but not limited to, gram-positive and gram-negative bacteria, fungi, protozoa and the like. The invention provides a method of treating or controlling a infection or contamination by such microorganisms or microbes comprising administering a therapeutically effective amount of at least one aminosterol compound of the invention, a derivative thereof, or a pharmaceutically acceptable salt thereof each as described above. According to a method of the invention, a host or tissue susceptible or afflicted with a microbial infection is treated with a therapeutically effective amount of at least one of the aminosterol compounds of the invention, its derivative or its pharmaceutically acceptable salt, each as described above. A "therapeutically effective amount," as described above, will be determined on a case by case basis upon routine experimentation as understood by of skill in the art. However, in general, a "therapeutically effective amount" is any amount sufficient to produce an antimicrobial or antibiotic effect in a susceptible or afflicted host or tissue. Alternatively, due to their antibiotic properties, the aminosterol compounds of the invention may also be used as a preservative or sterilizer of materials susceptible to microbial contamination.

The aminosterol compounds of the invention, its derivative or its pharmaceutically acceptable salt, each as described above, may also exhibit other activity including, but not limited to, antiangiogenic activity, direct inhibition of the growth of various cell types, appetite suppression, inhibition of an asthmatic response, inhibition of the sodium/proton exchanger NHE3, and localization of certain cell types or tissue types. Accordingly, the aminosterol compounds of the invention, its derivative or its pharmaceutically acceptable salt, each as described above, may be used in methods for: inhibiting angiogenic activity (e.g. inhibition of cancer growth and metastasis, inhibition of new blood vessel growth in the eye); directly inhibiting the growth of cells (e.g. endothelial cells, prostate tumor cells (in conjunction with VEGF) and melanomas); suppressing appetite resulting in, for example, weight loss and/or growth retardation; inhibiting an asthmatic response to an allergen; inhibiting the sodium/proton exchanger NHE3; or cell type or tissue type localization, preferably in some or all those cells or tissues involved in steroidogenesis or steroid metabolism.

The following examples are given to illustrate the invention. It should be understood, however, that the invention is not to be limited to the specific conditions or details described in these examples.

EXAMPLE 1

Isolation of Aminosterols from Dogfish Shark Liver

Twenty kilograms of fresh ground dogfish shark liver were suspended in 82 liters of 12% aqueous acetic acid at 75° C. for one hour. Eighteen kilograms of ammonium sulfate and seventeen liters of 95% ethanol were added followed by vigorous agitation for five minutes. The suspension was allowed to phase separate for six days at ambient temperature. The aqueous phase was then separated and filtered through cheesecloth. The combined filtrates from two such batches were slowly stirred with five kilograms XAD-16 resin (commercially available from Supelco of Bellefonte, Pa.) for twenty hours. The resin was collected, washed with ten liters of water and resuspended in twenty liters of 70% ethanol for approximately twenty minutes. An alcohol solution containing aminosterols (1)–(11) (see FIG. 1) was obtained following removal of the resin.

The alcohol solutions from ten shark liver preparations were combined (approximately 200 liters) and further filtered using a five micron polypure DCF filter (commercially available from Gelman Sciences of Ann Arbor, Mich.). The filtrate was loaded onto a three kilogram propylsulfonic acid column (commercially available from JT Baker of Phillipsburg, N.J.). The column was washed with 20% isopropyl alcohol until the adsorption at 254 nanometers (A254) reached a constant level. The column was washed with 0.4 M potassium acetate in 10% isopropyl alcohol until the A254 again reached a constant level. Aminosterol compounds (1)–(11) were successively eluted from the column with either 3.6 M or 4.5 M potassium acetate (pH 4) in 10% isopropyl alcohol (15–30 liters until A254 was constant). The 3.6 M and 4.5 M potassium acetate eluates contained different compositions or various mixtures of the aminosterols.

The 3.6 M and 4.5 M potassium acetate eluates were then separately filtered through 0.2 micron Sartopure GF capsules (commercially available from Sartorius of Edgewood, N.Y.), diluted with water to a 1.0 M salt concentration and loaded onto a 10×25 cm YMC-ODS column (commercially available from YMC of Wilmington, N.C.). Two buffers were used to elute the aminosterols from the column. Buffer A consisted of 0.1% trifluoroacetic acid in water while buffer B consisted of 0.1% trifluoroacetic acid in acetonitrile. The column was first washed at a flow rate of 470 milliliters per minute with forty liters of buffer A, then with ten liters of 25% buffer B. Aminosterols were then eluted from the column by a thirteen minute gradient from 25–34% buffer B followed by a twenty-two minute gradient from 34–40% buffer B. Five liter fractions were collected during the 25–34% elution followed by 235 milliliter fractions during the 34–40% elution. Side fractions containing less abundant aminosterols were pooled together according to their sequential elution order.

Each of the pools of aminosterols (approximately 35 liters) were separately loaded onto a 700 milliliter propyl-sulfonic acid column. The column was washed and the aminosterol compounds (1)–(11) eluted under the same conditions described above. The eluates of the 3.6 M and 4.5 M potassium acetate solutions were collected in two liter fractions and analyzed by thin-layer chromatography and HPLC. Fractions that contained a similar composition of aminosterols were combined while those that contained no aminosterols were discarded. If a combined mixture was not clear, the solution was ultra-filtered through a spiral membrane cartridge with a three kiloDalton cutoff (commercially available from Amicon of Wobum Mass.) to remove higher molecular weight residual pigments and proteins. The permeate was then loaded on a 1×25 cm YMC-ODS or 4×25 cm Dynamax (commercially available from Ranin of Woburn Mass.) column, washed with buffer A and eluted with an appropriate gradient of buffer B. Fractions were collected and analyzed by thin-layer chromatography. According to the thin-layer chromatography profile, fractions were further analyzed on an analytical reverse phase (RP) column using pre-column o-phthalaldehyde (OPA) derivatization. Pure fractions were combined, while those requiring further purification were purified using optimized chromatographic conditions. Final purifications were done on a Phenomenex Luna C18, Phenomenex phenyl-hexyl or Microsorb C18 columns (commercially available from Ranin of Woburn, Mass.).

EXAMPLE 2

Antimicrobial Activity of Aminosterols

Aminosterol compounds (1)–(11) were assayed in vitro against several microbial organisms to evaluate their spectrum of activity. Minimum inhibitory concentrations (MIC) for the bacteria and yeast were determined by incubating 0.9–1.1e5 colony-forming units per milliliter of log-phase microbes in 0.5×trypticase soy broth with increasing concentrations of sample in ninety-six well microtiter plates (commercially available from Corning of Corning, N.Y.) at 37° C. for eighteen to twenty-four hours. The minimum inhibitory concentration (MIC) is the lowest concentration of sample at which no growth was observed. Control incubation in the absence of bacteria served as a baseline value. Initial sample concentrations were two milligrams per milliliter in 250 mM sodium acetate, pH 6.6. Minimum inhibitory concentrations are summarized in Table 5.

TABLE 5

MIC Values for Aminosterol Compound (1)–(11)

| Aminosterol | S. aureus | E. coli | P. aeruginosa | C. albicans |
| --- | --- | --- | --- | --- |
| (1) | 8–16 µg/ml | 256 µg/ml | 256 µg/ml | 128 µg/ml |
| (2) | 31 µg/ml | 125 µg/ml | >250 µg/ml | |
| (3) | 250 µg/ml | >250 µg/ml | >250 µg/ml | |
| (4) | 4–8 µg/ml | 128 µg/ml | 32 µg/ml | 16 µg/ml |

TABLE 5-continued

MIC Values for Aminosterol Compound (1)–(11)

| Aminosterol | S. aureus | E. coli | P. aeruginosa | C. albicans |
| --- | --- | --- | --- | --- |
| (5) | 63 µg/ml | 125 µg/ml | 250 µg/ml | |
| (6) | 8 µg/ml | 63 µg/ml | >250 µg/ml | |
| (7) | 8–16 µg/ml | 16 µg/ml | 16 µg/ml | 32 µg/ml |
| (8) | 1 µg/ml | 8 µg/ml | 32 µg/ml | |
| (9) | 31 µg/ml | 31 µg/ml | 31 µg/ml | |
| (10) | 2 µg/ml | 8 µg/ml | 31 µg/ml | |
| (11) | 16 µg/ml | 125 µg/ml | 250 µg/ml | |

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art.

REFERENCES

Bibel, D. J., et al., "Antimicrobial activity of stratum corneum lipids from normal and essential fatty acid-deficient mice," *J Invest. Dermatol.* 92, 632–638, 1989.

Daly, J. W., et al., "Further classification of skin alkaloids from neotropical poison frogs (Dendrobatidae), with a general survey of toxic/noxious substances in the amphibia," *Toxicon.* 25, 1023–1095, 1987.

Ganz, T., et al., "Defensins. Natural peptide antibiotics of human neutrophils," *J. Clin. Invest.* 76, 1427–1435, 1985.

Jones, D. E., et al., "Paneth cells of the human small intestine express an antimicrobial peptide gene," *J. Biol. Chem.* 267, 23216–23225, 1992.

Kabara, J. J., et al., "Antimicrobial lipids: Natural and synthetic fatty acids and monoglycerides," *Lipids.* 12, 753–759, 1977.

Lee, J. Y. et al., "Antibacterial peptides from pig intestine: Isolation of a mammalian cecropin," *Proc. Natl. Acad. Sci. USA.* 86, 9159–9162, 1989.

Ouellette, A. J. et al., "Developmental regulation of cryptdin, a corticostatin-defensin precursor mRNA in mouse small intestinal crypt epithelium," *J. Cell Biol.* 108, 1687–1695, 1989.

Preusser, H. J. et al., "Antimicrobial activity of alkaloids from amphibian venoms and effects on the ultrastructure of yeast cells," *Toxicon.* 13, 285–289, 1975.

Steiner, H. et al., "Sequence and specificity of two antibacterial proteins involved in insect immunity," *Nature* 16, 292, 246–248, 1981.

Wehrli, S. L et al., "Structure of the novel steroidal antibiotic squalamine determined by two-dimensional NMR spectroscopy," *Steroids* 58, 370–378, 1993.

Zasloff, M., "Magainins, a class of antimicrobial peptides from Xenopus skin: isolation, characterization of two active forms, and partial cDNA sequence of a precursor," *Proc. Natl. Acad. Sci. USA* 84, 5449–5453, 1987.

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The claimed invention is:
1. A compound having the following structure:

or a pharmaceutically acceptable salt thereof.

2. A compound having the following structure:

or a pharmaceutically acceptable salt thereof.

3. A compound having the following structure:

or a pharmaceutically acceptable salt thereof.

4. A compound having the following structure:

or a pharmaceutically acceptable salt thereof.

5. A compound having the following structure:

or a pharmaceutically acceptable salt thereof.

6. A compound having the following structure:

or a pharmaceutically acceptable salt thereof.

7. A compound having the following structure:

or a pharmaceutically acceptable salt thereof.

8. A compound having the following structure:

or a pharmaceutically acceptable salt thereof.

9. A pharmaceutical composition comprising the compound of claim 1 and a pharmaceutically acceptable carrier.

10. A pharmaceutical composition comprising the compound of claim 2 and a pharmaceutically acceptable carrier.

11. A pharmaceutical composition comprising the compound of claim 3 and a pharmaceutically acceptable carrier.

12. A pharmaceutical composition comprising the compound of claim 4 and a pharmaceutically acceptable carrier.

13. A pharmaceutical composition comprising the compound of claim 5 and a pharmaceutically acceptable carrier.

14. A pharmaceutical composition comprising the compound of claim 6 and a pharmaceutically acceptable carrier.

15. A pharmaceutical composition comprising the compound of claim 7 and a pharmaceutically acceptable carrier.

16. A pharmaceutical composition comprising the compound of claim 8 and a pharmaceutically acceptable carrier.

17. A method of treating a microbial infection comprising administering a therapeutically effective amount of the compound of claim 1.

18. A method of treating a microbial infection comprising administering a therapeutically effective amount of the compound of claim 2.

19. A method of treating a microbial infection comprising administering a therapeutically effective amount of the compound of claim 3.

20. A method of treating a microbial infection comprising administering a therapeutically effective amount of the compound of claim 4.

21. A method of treating a microbial infection comprising administering a therapeutically effective amount of the compound of claim 5.

22. A method of treating a microbial infection comprising administering a therapeutically effective amount of the compound of claim 6.

23. A method of treating a microbial infection comprising administering a therapeutically effective amount of the compound of claim 7.

24. A method of treating a microbial infection comprising administering a therapeutically effective amount of the compound of claim 8.

* * * * *